United States Patent [19]

Allen et al.

[11] 4,393,264

[45] Jul. 12, 1983

[54] CONTINUOUS NON-CATALYTIC PYROLYSIS OF AQUEOUS SLURRY OF OXYGEN-CONTAINING DERIVATIVES OF BENZENE AND TOLUENE

[75] Inventors: John K. Allen, St. Charles; Gerard C. Lammers, Oswego, both of Ill.

[73] Assignee: Standard Oil Company (Indiana), Chicago, Ill.

[21] Appl. No.: 176,086

[22] Filed: Aug. 7, 1980

Related U.S. Application Data

[63] Continuation-in-part of Ser. No. 86,451, Oct. 19, 1979, abandoned.

[51] Int. Cl.$^3$ .............................................. C07C 1/20
[52] U.S. Cl. ................................................... 585/469
[58] Field of Search ....................................... 585/469

[56] References Cited

U.S. PATENT DOCUMENTS

| | | | |
|---|---|---|---|
| 3,775,296 | 11/1973 | Chervenak et al. | 585/469 X |
| 3,862,145 | 1/1975 | Brennan et al. | 585/469 X |
| 3,910,834 | 10/1975 | Anderson | 585/469 X |
| 4,097,541 | 6/1978 | Sakai et al. | 585/469 X |
| 4,258,227 | 3/1981 | Allen et al. | 585/469 |
| 4,266,084 | 5/1981 | Allen | 585/469 |

*Primary Examiner*—Paul F. Shaver
*Attorney, Agent, or Firm*—Gunar J. Blumberg; William T. McClain; William H. Magidson

[57] ABSTRACT

A solid mixture of aldehydo-, keto-, carboxy-, carboxy-and-aldehydo-, and keto-and-carboxy-substituted benzene and toluene especially as obtained as residue from the manufacture of benzene di- and tricarboxylic acid is continuously subjected to pyrolysis at a temperature above 700° C. with the production of a gaseous product and no substantial production of a solid carbonaceous char by adding such mixture as a suspension of comminuted solid in liquid water, but without an externally added catalyst, to a bed of inert, moving solids whose movement is stimulated by a gas flowing through said bed to fluidize, expand or make ebullient said bed of particles. Said gaseous product comprises hydrogen, carbon oxides, methane, benzene and toluene enriched in hydrogen and carbon dioxide content by the reaction of carbon and steam from the suspending liquid water thus substantially consuming the carbonaceous char which would otherwise be produced as a solid product. A source of molecular oxygen can be also advantageously added to the bed.

10 Claims, No Drawings

CONTINUOUS NON-CATALYTIC PYROLYSIS OF AQUEOUS SLURRY OF OXYGEN-CONTAINING DERIVATIVES OF BENZENE AND TOLUENE

RELATED APPLICATIONS

This application is a continuation-in-part of our co-pending patent application Ser. No. 86,451 which was filed on Oct. 19, 1979 and which is, now abandoned.

FIELD OF INVENTION

This invention relates to the non-catalytic pyrolysis of a solid mixture of oxygen-containing derivatives of benzene and toluene containing a cyclic ester group (e.g., as in phthalide) and one or more aldehydo-, methylol-, carboxy-nuclear substituents such as the solid residues obtained in the manufacture of an aromatic di- or tricarboxylic acid which also contain cobalt and/or manganese salts of organic acids and may also contain organic and inorganic bromides.

STATE OF THE ART

The thermal decomposition of benzoic acid to benzene and carbon dioxide begins non-catalytically at 370° C. in a glass bulb and is substantially complete as 400° C. (Chemical Abstracts, vol. 41, 646) according to the original article of Wolfgang Mosher in Helv. Chem. Acta. 14, 971–97 (1931) and such dissociation is accelerated by copper and cadmium catalysts. Said dissociation occurs at temperatures as low as 245° to 250° C. in the presence of Zn-Cu-Cr oxide-type catalysts according to Corliss R. Kinney and David P. Langlois in J. Am. Chem. Soc. vol. 53, 2189–2192 (1931). Decarbonylation of benzaldehyde to high yields of benzene is aided by plasma of glow discharge according to Published Patent Application ("Offenlegungsschrift") No. 2,038,272 of the Federal German Republic published Mar. 16, 1972. According to British Pat. No. 735,300 published Aug. 17, 1955, toluic acids heated to 400° C. in the presence of chromites of Zn, Cd, Zn-Cd, Zn-Fe or ZnO with either CuO or CdO are converted to toluene.

The preparation of benzoic acid by the thermal decarboxylation of phthalic acids in the presence of steam is known to be generally conducted in the presence of a catalyst such as nickel phthalate at 175° to 350° C. according to U.S. Pat. No. 1,962,175; 1 to 2% ammonia in the steam according to British Pat. No. 469,541 published July 27, 1932; $V_2O_5$ or ZnO on $Al_2O_3$ or $Al_2O_3$ alone according to Chemical Abstracts, vol. 37, Col. 5383; carbon catalyst impregnated with hydroxides of both alkali and alkaline earth metals to effect the decarboxylation at temperatures at and below 400° C. according to U.S. Pat. No. 2,470,688; cobalt carbonyl, $Co_2(CO)_8$ used in an atmosphere of carbon monoxide and hydrogen converts phthalic acids and substituted phthalic acids to benzoic acid and substituted benzoic acid or cobalt carbonyl modified by trialkylphosphine ligands converts benzene polycarboxylic acids having COOH groups on adjacent ring carbon atoms to iso- and terephthalic acids according to Chemical Abstracts, vol 81, entry 52064r. Also heating trimellitic acid to temperatures of 300° to 375° C. converts the tricarboxylic acid to o-phthalic acid according to U.S. Pat. No. 3,862,145.

From the state of the art at the time of making the present invention it appears that the main interest in decarboxylation of benzene carboxylic acids was to prepare a higher quality benzene carboxylic acid of lesser COOH group content from a benzene carboxylic acid of higher COOH group content and lower quality such as a coal acid or to obtain a benzene carboxylic acid of exceptionally high quality; e.g., pharmaceutical quality benzoic acid, from phthalic anhydride by converting it to o-phthalic acid and decarboxylating it. But there was no apparent interest in the decarboxylation of benzene carboxylic acids to aromatic hydrocarbons.

In an altogether different environment a new problem has arisen. In the commercial manufacture of benzene di- or tricarboxylic acids (e.g., isophthalic acid, terephthalic acid or trimellitic acid) there is obtained, after maximizing recovery of such acid and recovery for reuse the reaction solvent, a residue which is a mixture of oxygen-containing derivatives of benzene and toluene which are mono-, di- and tricarboxylic acids, aldehydo-carboxylic acids, and methylol-substituted benzene or toluene or their carboxylic (benzoic or toluic) acids and which also contains components of catalysis. Usually such components of catalysis are Co-Mn-Br or Co-Mn-Ce-Br from liquid phase oxidation of a xylene or pseudocumene (1,2,4-trimethylbenzene) with air in the presence of acetic acid reaction solvent. A similar residue is also obtained from the neat oxidation of liquid o-xylene with air in the presence of Co-Mn-Br catalyst system after dehydrating the o-phthalic acid formed to its anhydride under conditions which vaporize the anhydride, water and materials boiling between the anhydride and water. While such residues amount to from 2 to 25 weight percent of the benzene di- or tricarboxylic acid produced, such residue production annually is substantial in view of the millions of kilograms of the benzene di- or tricarboxylic acids produced annually.

Such residues contain water soluble benzene carboxylic acids and water soluble forms of the components of catalysis. Landfill disposal of such residues is undesirable because rain and ground water leach out those carboxylic acids and soluble forms of the components of catalysis and can contaminate surface run off water and eventually streams as well as below surface aquafiers. Disposal of such residues can be made by incineration and use made of the resultant heat produced but the catalyst components are converted to forms in the resultant ash which are difficult and/or expensive to convert to reusable forms for the oxidation of the methyl-substituted benzenes. Although in such residues the substituted benzene and toluene compounds whose substituents are the carboxy-, aldehydo- and methylol substituents are individually desirable and useful commercial products it is not economically feasible to separate and recover the individual compounds from the residues.

Based on the knowledge that most of the oxygen-containing aromatic compounds in the residue can be decaboxylated and/or decarbonylated by thermal means, it would be desirable to devise a decarboxylation and/or decarbonylation process which would convert the oxygen-containing aromatic compounds to aromatic hydrocarbons which are volatile under such process conditions so that the hydrocarbon vapors can be readily removed and condensed for their recovery. It is also known that under the severe thermal conditions required for substantially complete decarboxylation and/or decarbonylation to convert the oxygen-containing substituted aromatics to benzene and toluene there can also occur ring coupling (e.g. to form biphenyl) and ring fusion as well as charring of some of the organic compounds.

To use a decarboxylation and/or decarbonylation catalyst for the thermal conversion of the foregoing residues to easily recoverable and useful aromatic hydrocarbons would be desirable providing the use of catalyst does enhance the production of the aromatic hydrocarbons but does not make useless the resulting char or further contaminate the catalyst components present so as to make the recovery of cobalt, the most expensive component, technically and commercially unattractive.

We have in our laboratories investigated the use of various compositions previously suggested as decarboxylation catalyst and found the resulting thermal conversions to be unattractive.

There follows in TABLES I and II the results of vapor phase decarboxylation of a single benzene carboxylic acid by vaporizing the acid at one temperature and then contacting the vapors with a catalyst sometimes at a second temperature as indicated. Further, in such decarboxylation the catalyst is first placed in a quartz tube, the tube is heated in two zones with electric furnaces, and the benzene carboxylic acid sample is inserted into the vaporizing section of the tube in a ceramic boat, said boat is moved into and out of the vaporizing portion of the tube by a nichrome wire attached to the boar. Vaporization of the sample is accomplished in 5 to 15 minutes at the 500° C. temperature. A small nitrogen gas flow (about 3 ml/sec) through the tube is used to sweep the vapors through the hot catalyst and out of the tube. Products of the decarboxylations are collected by transport of the gaseous mixture after contact with the catalyst through two cooled traps, then through a drier to remove water vapor and then to a gas collector. At least one of the traps is cooled with a mixture of crushed solid $CO_2$ and isopropyl alcohol. Measured samples of the collected gas are analyzed by mass spectrometry. For the present purpose of illustrating the effectiveness of prior suggested catalysts, only the total amount of liquid aromatic hydrocarbons collected in the cooled traps and the amount of $CO_2$ generated expressed as weight percentages of the benzene carboxylic acid used are reported.

Except for two decarboxylations in TABLE I illustrating the use of zinc oxide and zinc oxide supported on alumina as the catalyst, the benzene carboxylic acid samples subjected to decarboxylation were about one gram in size. Those two exceptions used five gram samples supplied by five one gram samples successively introduced into the vaporizing portion of the tubes.

TABLE I
DECARBOXYLATION OF TEREPHTHALIC ACID

| | Catalyst | Temperature, °C. Vap. | Temperature, °C. Catalyst | Product, Wt. % Liquid | Product, Wt. % $CO_2$ |
|---|---|---|---|---|---|
| 4789-151 | Ba Promoted Cu Chromite | 352 | 352 | 3.97 | 64.5 |
| -150 | do | 399 | 399 | 7.99 | 127.7 |
| -156 | $Cu_2O_3$—ZnO | 400 | 400 | 11.9 | 102.3 |
| -147 | Ni Oxide on Alumina | 446 | 446 | 18.0 | 45.4 |
| -155 | ZnO | 511 | 511 | 24.0 | 39.9 |
| -165 | ZnO—Chromia | 499 | 499 | 35.8 | 49.2 |
| -184 | Zn Chromite | 499 | 499 | 21.8 | 67.9 |
| -185 | Chromia-Alumina-Magnesia | 500 | 500 | 17.7 | 46.3 |
| -188 | K Promoted Chromia-Alumina | 499 | 499 | 20.8 | 66.1 |
| -195 | ZnO—Alumina | 498 | 498 | 33.9 | 29.0 |
| -200 | ZnO—$MoO_2$ on Molecular Sieve | 499 | 499 | 31.7 | 26.8 |
| -204 | ZnO—$Co_2O_3$—$W_2O_3$ on Molecular Sieve | 500 | 500 | 33.0 | 48.8 |
| 5065-001 | ZnO—$Co_2O_3$—$MoO_2$ on Molecular Sieve | 500 | 500 | 22.0 | 39.3 |
| -005 | Chromia on Molecular Sieve | 499 | 499 | 17.0 | 41.3 |
| -006 | ZnO* | 501 | 501 | 24.3 | 23.0 |
| -007 | ZnO on Alumina* | 500 | 500 | 32.9 | 36.3 |
| -010 | ZnO—Alumina | 500 | 500 | 33.0 | 47.9 |
| -022 | do | 499 | 498 | 36.9 | 47.3 |
| -023 | do | 501 | 399 | 0 | 19.9 |
| -025 | do | 500 | 451 | 26.9 | 40.6 |
| -030 | CaO | 500 | 502 | 25.9 | 0.04 |
| -031 | $CaCO_3$ | 499 | 501 | 5.0 | 29.9 |
| -036 | CdO | 499 | 502 | 22.0 | 38.8 |

*Five grams terephthalic acid

The theoretical amounts of benzene and carbon dioxide from the complete decarboxylation of terephthalic acid are, respectively, 47 weight percent and 53 weight percent. The above amounts of $CO_2$ reported in excess of said 53 wt.% may be from partial combustion of the benzene produced.

TABLE II
DECARBOXYLATION AND/OR DECARBONYLATION OF BENZOIC ACID AND SUBSTITUTED BENZOIC ACIDS IN THE PRESENCE OF ZINC OXIDE ON ALUMINA

| | Acid | Temperature, °C. Vap. | Temperature, °C. Catalyst | Product, Wt. % Liquid | Product, Wt. % $CO_2$ |
|---|---|---|---|---|---|
| 4789-149 | Benzoic Acid* | 399 | 399 | 19.9 | 12.26 |
| 5065-037 | Benzoic Acid | 501 | 501 | 53 | 29.7 |
| -011 | Isophthalic Acid | 500 | 500 | 33 | 45.4 |
| -012 | o-Phthalic Acid | 497 | 499 | 24 | 37.2 |
| -014 | p-Toluic Acid | 501 | 501 | 21 | 21 |
| -015 | Trimellitic Acid | 502 | 502 | 13 | 32.8 |
| -016 | 4-Carboxybenzaldehyde | 500 | 500 | 18.4 | 31.1 |
| -017 | Phthalic Anhydride | 502 | 502 | 20 | 36 |
| -035 | Trimellitic Acid Anhydride | 499 | 500 | 12.8 | 53.2 |

*Catalyst is Ni Oxide on Alumina

In TABLE III to follow terephthalic acid process residue (TAR), hereinafter more completely defined, unextracted or water extracted (TARX) is decarboxyl- and decarbonylated in the presence of various catalysts at various temperatures. Again only the total liquid aromatic hydrocarbons and $CO_2$, both in weight percent of sample, are reported. Also a slight flow (about 3 ml/sec) of nitrogen gas is used for the purposes before described.

TABLE III
DECARBOXYLATION AND DECARBONYLATION OF TEREPHTHALIC ACID PROCESS RESIDUES

| | Catalyst | Temperature, °C. Vap. | Temperature, °C. Catalyst | Product, Wt. % Liquid | Product, Wt. % $CO_2$ |
|---|---|---|---|---|---|
| 4789-124 | Copper Wool | 353 | 353 | 0 | 2.29 |
| -125 | $Cu_2O$-wire | 350 | 350 | 0 | 10 |
| -126 | " | 400 | 400 | 0 | 16.6 |

TABLE III-continued
DECARBOXYLATION AND DECARBONYLATION OF TEREPHTHALIC ACID PROCESS RESIDUES

| Catalyst | | Temperature, °C. | | Product, Wt. % | |
|---|---|---|---|---|---|
| | | Vap. | Catalyst | Liquid | $CO_2$ |
| -134 | Ba Promoted Cu Chromite | 500 | 500 | 0 | 105.6 |
| -132 | Gamma Alumina | 500 | 500 | 0 | 19.8 |
| -128 | Chromia on Gamma Alumina | 400 | 400 | 0 | 14.5 |
| -136 | ZnO—Alumina Co Gel | 500 | 500 | 0 | 3.58 |
| -137 | Chromia Promoted $Fe_2O_3$ | 400 | 400 | 0 | 18.4 |
| -131 | Co—Molybdate on Gamma Alumina | 397 | | 0 | 1.64 |
| -142 | $Co_2O_3$ on Keiselguhr | 398 | 398 | 0 | 30.34 |
| -145 | Ni Oxide on Refractory Support | 399 | 399 | 10.96 | 15.8 |
| -171 | ZnO | 499 | 499 | 28.0 | 23.4 |
| -196 | ZnO on Alumina | 500 | 500 | 26.0 | 22 |
| 5065-009[1] | ZnO on Alumina | 499 | 499 | 26.2 | 30.0 |
| -008[1,2] | ZnO on Alumina | 502 | 502 | 27.7 | 26.2 |
| -041[3] | ZnO on Alumina | 501 | 501 | 24.0 | 26.7 |
| -044[4] | ZnO on Alumina | 501 | 501 | 28.0 | 31.0 |
| -026[2] | ZnO on Alumina | 501 | 502 | 30 | 35.8 |
| -027 | ZnO on Alumina | 503 | 500 | 26 | 36.4 |
| -034[5] | ZnO on Alumina | 499 | 504 | 22.9 | 40.4 |

[1]Sample is five grams
[2]Residue from terephthalic acid process after being extracted with water.
[3]Sample is 40.76 grams
[4]Sample is 28.85 grams
[5]Residue from o-phthalic acid process after being extracted with water.

In general, the use of prior suggested decarboxylation catalysts did cause carbon dioxide to be liberated or produced but not all such catalysts caused an attractive co-production of liquid aromatic hydrocarbons. Of those prior suggested decarboxylation catalysts, zinc oxide alone, or zinc oxide in admixture with or supported by chromia or alumina, or a mixture of zinc oxide with either molybdena, or with oxides of cobalt and tungsten supported on molecular sieves in general were found to produce liquid aromatic hydrocarbons in yields upward from about 50 percent of the theoretical yield at temperatures above 450° C. However, the effective life of such better liquid aromatic hydrocarbon producing catalyst was short.

The consistently better prior suggested catalyst was found to be the combination of zinc oxide and alumina. Such catalyst is used at 500° C. with one to two gram samples of terephthalic acid process residues introduced consecutively at about 5-minute intervals into the heated quartz tube containing said catalyst over a five day period. The liquid aromatic hydrocarbon yield decreases from 26.4 weight percent down to 14.6 weight percent of residue fed over the five day period and considerable blackening of the catalyst is observed. Said liquid aromatic hydrocarbon decrease occurs with a residue to catalyst weight ratio of no more than about 2:1. Such results indicate a very short life for the ZnO-alumina catalyst and that frequent regeneration thereof would be necessary for such catalyst to be used commercially.

Such short useful catalyst life made the use thereof for pyrolysis of the aforementioned residues commercially unattractive. However the present inventive non-catalytic continuous pyrolysis of the oxygen-containing derivatives of benzene and toluene and especially the cyclic ester, methylol-, aldehydo-, carboxy-, carboxy- and aldehydo-, keto-and-carboxy-and methylol-and-carboxy substituted benzenes obtained as a residue from the manufacture of benzene di- and tricarboxylic acids does not have such disability and is technically and commercially attractive.

STATEMENT OF THE INVENTION

According to the present invention a solid mixture of cyclic ester containing an aldehydo-, methylol-, carboxy-, keto-and-carboxy-, methylol-and-carboxy, and carboxy-and-aldehydo-substituted benzene and toluene and such mixtures from the manufacture of benzene di- and tricarboxylic acids also containing cobalt salt or cobalt and manganese salts of organic acids and, further, sometimes containing organic or inorganic bromides is in particulate form suspended in water, mixed with an inert inorganic solid in like particulate form, and the resulting mixture of particulates is passed through a pyrolysis zone maintained at a temperature of at least 700° C. There exits such pyrolysis zone only a gaseous mixture of carbon oxides, hydrogen, methane, $C_2$ alkanes and alkenes together with oxygen-containing aliphatics, vapors of water, benzene, toluene, and multi-ring aromatic hydrocarbons (biphenyl, terphenyl and anthracene).

The aqueous suspension of the aforementioned solids can contain from 20 weight percent up to 50 weight percent water and 80 to 50 weight percent solids. Such suspensions are mixed with the inert, inorganic particles in a bed thereof which is fluidized, expanded or made ebullient by a gas inert to the bed's particles. Such non-quiescent forms of beds of particles are art recognized as advantageously useful beds of particulate solids for gas-liquid and gas-gas contact when the particulates are catalyst. Preferred for the conduct of this present inventive process are the use of particles of silica sand having a particle size (diameter) not larger than 0.8 mm down to 0.2 mm for mixing with the above solid oxygen-containing mixture of aromatic compounds suspended in water. For the purposes of this invention such mixture of solid oxygen-containing aromatic compounds suspended in water have a particle size of from 0.83 mm down to 0.58 mm diameter.

The reactor can have an internal gas-solid disengaging zone for separation of gases and vapors from the bed's particles. The mixture of particles, gases and vapors can be permitted to flow out of the reactor into a cyclone separator from which an overhead gas-vapor mixture separates and discharges and from which the solid particles are discharged as underflow. The bed of particles can be fluidized, expanded or made ebullient by nitrogen, argon or air, air enriched with oxygen gas, or oxygen gas added separately or with the aqueous slurry of the comminated solid mixture of the before named oxygen-containing derivatives of benzene and toluene.

The use of a suspension of such oxygen-containing derivatives of benzene and toluene with the bed of non-quiescent inert particulates in the pyrolysis process of this invention results in little or no carbonaceous char formation. Rather the carbon of such char appears to react (as the char forms) with the steam (from vaporizing the water of the suspension) present according to the well-known water-gas reaction:

$$C + 2H_2O \rightarrow CO_2 + 2H_2$$

Such water-gas reaction increases the hydrogen content of the gaseous product of the present invention. Also there is an attendant increase in the carbon dioxide content of the gaseous product. The advantages of additional hydrogen production and disappearance of the carbonaceous char are believed to offset the increased carbon dioxide content of the gaseous product which either with or without separation of benzene and toluene can be burned to provide heat for the pyrolysis.

Also oxygen gas or air, or air encriched with oxygen can be added alone or admixed with an inert gas (e.g. nitrogen) and used to fluidize, expand or make enbullient the bed of particulates to burn some of the gaseous product and provide heat for the non-catalytic pyrolysis of this invention. Quite surprisingly, such use of oxygen during the pyrolysis results in only a small (15 to 20%) loss of the benzene and toluene but does cause a substantial decrease in the yield of methane, hydrogen and carbon monoxide. Such decrease in yields of $CH_4$, $H_2$ and CO is unexpected because it is greater than the loss which can be calculated from the oxygen consumed.

We have observed that non-catalytic pyrolysis at temperatures of 700° C. and above conducted with residues from the manufacture of benzene di- and tricarboxylic acids and in the absence of steam, in general, produce a carbonaceous char in a yield of from 8 up to 18 weight percent of the residue. Typically such carbonaceous char product contains 60 weight percent carbon. Complete utilization of the carbon content of such char product in the water-gas reaction would require from 11.5 up to 25 weight percent water in the slurry fed to the present inventive non-catalytic pyrolysis in a bed of actively moving inert particulates.

The present inventive continuous non-catalytic pyrolysis produces a gaseous product which, in addition to the carbon oxides from decarboxylation and decarbonylation and carbon dioxide and hydrogen from the water-gas reaction, contains water vapor, hydrogen, methane, benzene, toluene and multi-ring aromatics such as biphenyl, terphenyl and anthracene.

Residues from the manufacture of benzene di- and tricarboxylic acids which are the preferred solids fed to the present inventive non-catalytic pyrolysis, in general, contain from zero to five weight percent total of water and acetic acid, from three up to five weight percent total of components of catalyst and associated with the metals (usually in the plus two valence state) from three to ten weight percent acetate radical. Thus, the oxygen-containing aromatic compounds can comprise from 79 to 96 weight percent of the residue.

More specifically, the oxygen-containing aromatic compounds which can be present in the residues subjected to pyrolysis of this invention can be illustrated by the identified compounds present in the residue from the manufacture of terephthalic acid by the air oxidation of p-xylene in acetic acid as reaction solvent and in the presence of cobalt, manganese and bromine as components of the catalyst system. Such identified compounds are now known to be: terephthalic acid and its precursors p-toluic acid, p-formylbenzoic acid, p-tolualdehyde, terephthalaldehyde and p-methylbenzyl alcohol by-products including methylphthalic acids, ortho- and isophthalic acids (from o- and m-xylene impurities in the p-xylene), trimellitic acid, as well as benzaldehyde and benzoic acid (from ethylbenzene impurity in p-xylene); and co-products including 4,4'-bibenzoic acid; 1,2-bis (p-carboxyphenyl) ethane; 2,5,4'-tricarboxybiphenyl; 2,6-dicarboxyfluorenone; and 4,4'-stilbene dicarboxylic acid. On a water- and acetic-acid free basis one such residue contains the weight percentages of the foregoing compounds and groups of compounds as shown in TABLE IV to follow.

TABLE IV

| COMPONENTS OF RESIDUE FREE OF WATER AND ACETIC ACID | |
|---|---|
| Terephthalic Acid | 26.4% |
| p-Toluic Acids | 20.8% |
| p-Formylbenzoic acid | 9.1% |
| p-Tolualdehyde | 0.51% |
| Terephthalaldehyde | 1.20% |
| p-Methylbenzyl Alcohol | 2.06% |
| Reaction By-Products | 36.9% |
| Co-Products | 4.12% |

Another such residue has the composition including the catalyst components: cobalt, manganese and bromine and metals of corrosion as shown in TABLE V to follow.

TABLE V

| RESIDUE FROM TEREPHTHALIC ACID MANUFACTURE ON ACETIC ACID AND WATER-FREE BASIS | |
|---|---|
| Component | Weight Percent |
| Phthalic Acids | 19.0 |
| Benzoic Acid | 14.8 |
| Toluic Acids | 26.7 |
| Methyl Phthalic Acids | 2.65 |
| Trimellitic and Trimessic Acids | 4.32 |
| 4-Carboxybenzaldehyde | 9.09 |
| Tolualdehydes | 0.40 |
| Benzaldehyde | 0.004 |
| Terephthalaldehyde | 0.27 |
| Methylbenzyl Acetate | 0.02 |
| Formyl Acetate | 0.15 |
| Benzylbenzoate | 0.07 |
| Phthalide | 2.04 |
| Co-Products | 4.24 |
| Cobalt | 1.51 |
| Manganese | 2.53 |
| Bromine | 2.20 |
| Iron | 0.09 |
| Aluminum | 0.00022 |
| Calcium | 0.02 |
| Chromium | 0.007 |
| Copper | 0.0001 |
| Magnesium | 0.0028 |
| Molybdenum | 0.0035 |
| Sodium | 0.30 |
| Nickel | 0.0052 |
| Silica | 0.0025 |
| Anion of Metals | 9.04 |

The first four elements are determined by X-ray fluorescence and the remaining elements are determined by emission spectroscopy. The foregoing more detailed identification of organic components and metals is not one usually made by terephthalic acid manufacturing facilities but is made for research purposes as a starting point, for example, to identify extractable components, or to evaluate the completeness of commercial oxidation of the xylene feed, or to evaluate potential increase of phthalic acids production by some additional oxidation of the phthalic acid precursors present in such residue.

However, the terephthalic acid manufacturing facilities will obtain a partial analysis of the residue to include at least the phthalic acids, toluic acids, benzoic acid and catalyst components to determine on a day-to-day basis the approximate oxidation efficiency, and catalyst metal and solvent discard. Such partial analytical inspections of the residue are as shown in TABLE VI to follow.

TABLE VI
PARTIAL ANALYTICAL RESULTS OF RESIDUE FROM TEREPHTHALIC ACID MANUFACTURE

| Components | Sample Number | | | |
|---|---|---|---|---|
| In Weight % | 1 | 2 | 3 | 4 |
| Acetic Acid | 0.22 | 3.23 | 3.74 | 3.24 |
| Phthalic Acids | 45.8 | 31.4 | 33.4 | 26.0 |
| Toluic Acids | 5.2 | 12.3 | 12.9 | 22.6 |
| 4-CBA[1] | 1.05 | 4.56 | 4.82 | 9.1 |
| Benzoic Acid | 20.2 | 27.6 | 26.0 | 19.8 |
| Trimellitic Acid | 0.2 | 4.0 | 4.3 | 3.8 |
| OLB Compounds[2] | — | 4.1 | 4.4 | 0.9 |
| HB Compounds[3] | 0.26 | 7.5 | 5.8 | 0.4 |
| Cobalt | 0.69 | 0.49 | 0.5 | 1.35 |
| Manganese | 1.79 | 1.22 | 1.3 | 2.48 |
| Bromine | 2.59 | 1.49 | 1.5 | 2.5 |

[1] "4-CBA" is 4-carboxybenzaldehyde (p-formylbenzoic acid).
[2] "OLB Compounds" are other lower boiling compounds.
[3] "HB Compounds" are higher boiling (higher than trimellitic acid) compounds.

The residue from manufacture of isophthalic acid by air oxidation of m-xylene in an acetic acid reaction medium and in the presence of catalysis provided by cobalt, manganese and bromine is quite similar to the residue from the manufacture of terephthalic acid by the same oxidation of p-xylene. The manufacture of the anhydride (intramolecular) of trimellitic acid (TMA) can produce two residues. One residue is obtained after precipitating and separating impure trimellitic acid from the acetic acid solution of the catalyst (Co-Mn-Br) system and then evaporating the acetic acid. The second residue is obtained after dehydration of impure trimellitic acid (TMLA) to its impure anhydride and evaporating a partially purified anhydride. The compositions of such TMLA and TMA residues and the residue from isophthalic acid (IA) manufacture are characterized in TABLE VII to follow.

TABLE VII
CHARACTERIZATION OF RESIDUES FROM THE MANUFACTURE OF ISO-PHTHALIC ACID AND TRIMELLITIC ANHYDRIDE

| Component, | RESIDUE | | |
|---|---|---|---|
| In Weight % | IA | TMLA | TMA |
| Acetic Acids | 0.11 | 1.58 | 0 |
| Phthalic Acids | 39.8 | 12.3 | 1.0 |
| Toluic Acids | 1.8 | 0 | 0 |
| Aldehydes | 0.09 | 0.53 | 1.4 |
| Benzoic Acid | 24.1 | 0.5 | 0 |
| Trimellitic Acid | 2.5 | 38.6 | 65.2[1] |
| OLB Compounds[2] | 1.7 | 4.7 | 1.9 |
| HB Compounds[2] | 5.3 | 0.94 | 0.4 |
| Cobalt | 0.48 | 1.17 | 2.51 |
| Manganese | 1.27 | 0.28 | 0.87 |
| Bromine | 2.6 | 0.94 | 0.15 |

[1] Trimellitic acid anhydride
[2] See TABLE VI

The residues from the manufacture of phthalic anhydride of interest for use in the practice of the present invention are obtained from two different oxidation processes. The residue from the first of such processes is obtained after evaporation of acetic acid and water from the liquid portion of the oxidation effluent from the air oxidation of o-xylene in an acetic acid solution of the Co-Mn-Br catalyst system after precipitating and recovering o-phthalic acid or its anhydride from the oxidation effluent. Such residue contains the components and their concentrations substantially the same as in the residues characterized by TABLES VI through VII. The residue from the second type of oxidation process is obtained by heating the oxidation effluent to convert o-phthalic acid to its anhydride and evaporate the anhydride and water when such effluent is produced by the air oxidation of liquid o-xylene in liquid o-phthalic acid containing the Co-Mn-Br system of catalysis. Since such oxidation does not use an extraneous solvent, it is hereafter sometimes referred to as the "neat oxidation" process. Such residue from the second type of oxidation process comprises 50 to 85 weight percent phthalic anhydride as a flux for higher boiling materials; e.g., iso- and terephthalic acid, trimellitic acid, metal (Co and Mn) phthalates or acetates, and oxygen-containing both coupled and fused ring compounds: di-, tri- and tetracarboxy-substituted biphenyl and benzophenone and dicarboxyfluorenone. In TABLE VIII to follow there are given the components and their concentrations in weight percent of such residues from said second type of o-xylene oxidation process.

In TABLE VIII "PAN" is used to designate phthalic anhydride and "2-CBA" is used to designate 2-carboxybenzaldehyde.

TABLE VIII
NEAT OXIDATION RESIDUES

| Component | Residue Number | | | | |
|---|---|---|---|---|---|
| Weight % | 1 | 2 | 3 | 4 | 5 |
| PAN | 72.2 | 77.4 | 65.7 | 84.5 | 57.3 |
| o-Toluic Acid | 0.03 | 0.23 | 0.15 | 0.04 | 0.1 |
| Phthalide | 0.01 | 0.2 | 0.18 | 0.001 | 0.3 |
| 2-CBA | 0.77 | 1.0 | 1.03 | 0.41 | 1.65 |
| Benzoic Acid | 0.56 | 1.03 | 0.69 | 0.60 | 1.8 |
| Other Aromatics | 20.7 | 16.0 | 26.8 | 11.5 | 22.7 |
| Cobalt | 1.14 | 1.08 | 1.36 | 0.62 | 0.58 |
| Manganese | 3.38 | 2.29 | 3.34 | 1.85 | 1.13 |
| Bromine | 1.32 | 0.90 | 0.78 | 0.87 | 1.01 |

Also useful in the practice of the present inventive pyrolysis are the undissolved solids portion of the residues after the extraction of the residues with water to remove catalyst metals for reuse in the oxidation from which the metal-containing residue originated. Such undissolved solids portion is hereafter referred to as "extracted residue". In TABLE IX to follow characteristics of such extracted residues are given.

TABLE IX
EXTRACTED RESIDUES

| Components Weight % | Of Sample 1 TABLE VI | Of Sample 3 TABLE VI | Of Neat Oxidn. Residue |
|---|---|---|---|
| Aldehydes | 1.57 | 5.84 | 1.03 |
| Benzoic Acid | 18.1 | 31.4 | 1.7 |
| Toluic Acids | 1.61 | 16.0 | 0 |
| Phthalic Acids | 56.4 | 37.6 | 5.6 |
| OLB Compounds | 0.4 | 0.78 | 41.0 |
| HB Compounds | 8.0 | 3.6 | 0.2 |
| Cobalt | 0.18 | 0.03 | 0.16 |
| Manganese | 0.49 | 0.10 | 0.28 |
| Bromine | 0.51 | 0.09 | 0.35 |

Conduct of the present inventive continuous non-catalytic pyrolysis is illustrated by the use of a fluidized bed of 3558 grams of silica and particles having a size of from 0.210 up to 0.297 mm diameter. Said bed of silica sand is contained in a vertical stainless steel (316 S.S.) pipe of 101.6 mm internal diameter, 3.175 mm wall thickness and 1220 mm length. The sand is contained in the lower 305 mm length of the pipe. The pipe is heated by variable energy input external electric resistance heaters fastened to the outer wall of the pipe. The lower end of the pipe is fastened to an inverted cone of 316 S.S. stainless steel. The apex of the conical bottom of the apparatus is fitted with an inlet for charging a gas to fluizide the silica bed. The cone also has a slurry feed inlet near the junction of the inverted cone and the pipe to which there can be directly attached either a feed tube or a modified feed tube extending into and through said feed inlet upwardly into the bed and terminating about 100 mm above the junction of the cone and pipe. The feed tube connected directly to the slurry feed inlet to the cone is used when the carrier gas is nitrogen. The feed tube which extends into the bed is used when air and nitrogen or oxygen and nitrogen comprise the fluidizing gas to decrease the chance of combustion of the aromatic (benzene and toluene) hydrocarbon products. Both slurry feed tubes at a point prior to their attachment to or entry in the feed inlet have connections for a valved steam line so that steam can be injected with the feed slurry, if necessary, to maintain its temperature and thaf of the feed tube at or slightly above 80° C.

The upper 915 mm of the vertical pipe functions as a gas-solids disengager zone. The top of the pipe is attached to a vapor-gas transfer line which is tapped for a sampling line of 316 S.S. type stainless steel tubing having a 4.93 mm internal diameter and a 0.71 mm wall thickness. Said sampling line is attached to the inlet of a vertical down flow water cooled condenser about 1830 mm long fitted to a condensate receiver which in turn is attached to a particulate trap and then to a vacuum pump which discharges through a wet test meter of from 0 up to 453 standard liters per hour wet gas flow. The wet test meter in turn discharges into an on line gas chromatograph unit having both flame ionization and thermal conductivity detectors. Nitrogen is used as the internal standard in said unit. Such gas chromatograph unit has the capability of performing a complete gas analysis for $H_2$, $N_2$, CO, $CO_2$, $CH_4$, $C_6H_6$ and $C_7H_8$ from one sample.

The operating conditions and results therefrom are hereafter reported in TABLES X and XI wherein "TAR" is residue from terephthalic acid residue.

TABLE X

NON-CATALYTIC PYROLYSIS OF TAR SUSPENDED IN WATER IN BED OF SILICA PARTICLES FLUIDIZED WITH NITROGEN GAS

| Example No. | 1 | 2 | 3 | 4 |
|---|---|---|---|---|
| Suspension: | | | | |
| Water, wt. % | 30 | 30 | 30 | 30 |
| TAR wt. % | 70 | 70 | 70 | 70 |
| Operating Conditions: | | | | |
| Temperature, °C. | 710 | 755 | 730 | 740 |
| TAR, gms/hr. | 1200 | 1800 | 1600 | 1100 |
| $N_2$, gms/hr. | 730 | 730 | 730 | 730 |
| Product Component Yield: | | | | |
| $H_2$, wt. % | 3.2 | 4.1 | 1.6 | 4.9 |
| CO, wt. % | 10.4 | 26 | 9.7 | 32 |
| $CO_2$, wt. % | 60 | 34 | 73 | 80 |
| $CH_4$, wt. % | 4.4 | 2.3 | 0.7 | 0.5 |
| $C_6C_6$, wt. % | 28 | 34 | 42 | 35 |
| $C_7H_8$, wt. % | 1.7 | 4.5 | 2.5 | 2.8 |
| Char Yield: | | | | |
| Actual, wt. % | — | — | — | 0.86 |
| Prior Experience, wt. % | 8–10 | 8–10 | 8–10 | 8–18 |

TABLE XI

NON-CATALYTIC PYROLYSIS OF TAR SUSPENDED IN BED OF SILICA PARTICLES FLUIDIZED WITH NITROGEN AND AIR FED

| Example No. | 5 | 6 |
|---|---|---|
| Suspension: | | |
| Water, wt. % | 30 | 30 |
| TAR, wt. % | 70 | 70 |
| Operating Conditions: | | |
| Temperature, °C. | 770 | 770 |
| TAR, gms/hr. | 1100 | 1100 |
| $N_2$, gms/hr. | 590 | 590 |
| $O_2$, gms/hr. | 170 | 170 |
| Product Component Yield: | | |
| $H_2$, wt. % | 0.073 | 0.16 |
| CO, wt. % | 4.3 | 3.81 |
| $CO_2$, wt. % | 60 | 58.1 |
| $CH_4$, wt. % | 0.34 | 0.14 |
| $C_6H_6$, wt. % | 30 | 28 |
| $C_7H_8$, wt. % | 1.9 | 1.0 |
| Char Yield Actual, wt. % | 0.26 | 0.26 |

In addition to the benzene and toluene produced by the processes of Examples 5 and 6, when air is added to the the nitrogen fluidizing gas, there is also produced a higher molecular weight liquid aromatic mixture which contains small amounts of benzoic acid, benzaldehyde benzophenone, benzylbenzoate and a relatively large amount of an unknown compound which eluted in the phthalide area.

The process of Examples 5 and 6, it will be appreciated, used very little nitrogen with the air feed.

The following three examples, although presented together in tabulated form, are conducted consecutively with each exemplary process being conducted upon noting the successful operation of the preceding example. Thus Example 7 is conducted using air alone for the added gas for fluidizing, ebulating or expanding of the bed of inert, particulated solids, here the 3558 grams of silica sand whose particles have a size of from 0.210 up to 0.297 mm in diameter used in the apparatus described in regard to the conduct of Examples 5 and 6.

EXAMPLES 7, 8 AND 9

In each of these three illustrative examples the apparatus used for Examples 5 and 6 is again used. To the feed tube extending into the bed and terminating about 100 mm above the inverted cone there is feed 1589 grams per hour of a slurry comprising 1021.5 grams of terephthalic acid process residue (TAR) and 567.5 grams per hour of water. This slurry is at a temperature of 93° C. as it is pumped into the slurry feed inlet. The gas fluidizing the bed of silica particles is at a temperature of 17.5° C. and is air (21 vol. % oxygen in Example 7), air enriched with oxygen gas to 26 volume percent oxygen (Example 8) and oxygen gas (Example 9). The amounts of such gas in kilograms per hour of the gaseous components ($O_2$ and $N_2$ only) are given in TABLE XII to follow together with the amount of char produced as a weight percent of TAR fed, and the components of the gas-vapor product and mixtures as weight percent thereof.

TABLE XII

NON-CATALYTIC PYROLYSIS OF TAR SUSPENSION IN BED OF SILICA PARTICLES FLUIDIZED WITH AIR, $O_2$ ENRICHED AIR, OR OXYGEN GAS FED AT 17.5° C.

Bed Temperature: 760° C. Suspension Temperature: 93° C.
Suspension Feed Rate: 1598 grams per hour containing TABLE XII-continued
NON-CATALYTIC PYROLYSIS OF TAR SUSPENSION
IN BED OF SILICA PARTICLES FLUIDIZED
WITH AIR, $O_2$ ENRICHED AIR,
OR OXYGEN GAS FED AT 17.5° C.

| 1021.5 grams TAR and 567.5 grams water | | |
|---|---|---|
| Example No. 7 | Example No. 8 | Example No. 9 |
| Gas Feed: Air | Gas Feed: 26 vol. % $O_2$; | Gas Feed, $O_2$ gas |
| $O_2$: 390.4 grams/hr | $O_2$: 364.3 grams/hr | $O_2$: 307 grams/hr |
| $N_2$: 1286.5 grams/hr | $N_2$: 908 grams/hr | $N_2$: 0 grams/hr |
| PRODUCTS | PRODUCTS | PRODUCTS |
| Gas-vapor | Gas-vapor | Gas-vapor |
| $H_2$ 0.106 wt. % | $H_2$ 0.12 wt. % | $H_2$ 0.184 wt. % |
| $CO_2$ 26.9 wt. % | $CO_2$ 29.7 wt. % | $CO_2$ 41.8 wt. % |
| CO 1.36 wt. % | CO 1.55 wt. % | CO 2.36 wt. % |
| $CH_4$ 0.176 wt. % | $CH_4$ 0.22 wt. % | $CH_4$ 0.306 wt. % |
| $N_2$ 39.9 wt. % | $N_2$ 32.2 wt. % | $N_2$ 0 wt. % |
| Water 20.6 wt. % | Water 23.4 wt. % | Water 34.9 wt. % |
| Toluene 1.6 wt. % | Toluene 1.83 wt. % | Toluene 2.70 wt. % |
| Benzene 9.35 wt. % | Benzene 10.99 wt. % | Benzene 17.2 wt. % |
| Solid char | Solid char | Solid char |
| 4.06 wt. % of TAR | 4.06 wt. % of TAR | 4.06 wt. % of TAR |

It was determined prior to Example No. 9 that the water content of the TAR suspension would, when converted to water vapor, produce the necessary vapor to fluidize, ebulate or expand the bed of sand particles. It was also appreciated that the same water vapor could initially, before the oxygen was otherwise consumed, at least supress combustion of toluene and benzene.

The invention claimed is:

1. A continuous method of non-catalytic pyrolysis of a solid mixture comprising aldehydo-, keto, carboxy-, aldehydo-and-carboxy-, keto-and-carboxy-, and methylol-and-carboxy-, substituted benzenes and toluenes to decarboxylate and decarbonylate such mixture which comprises adding a suspension of comminuted solid mixture of said substituted benzenes and toluenes in water, but without an externally added catalyst, to a bed of inert, non-catalytic particulated solids which can be fluidized, expanded or made ebullient with the flow of a gas through said bed wherein said bed is heated to a temperature of at least 700° C. and the gas stimulating said movement of the particles in the bed is nitrogen, air, or a mixture of nitrogen and air, or a mixture of air and oxygen gas, or oxygen gas alone or in admixture with steam.

2. The continuous pyrolysis process of claim 1 wherein the solid mixture of oxygen-containing benzenes and toluenes also contains a cobalt salt of organic acids.

3. The process of claim 1 wherein the bed of particulated solid is a bed of silica sand.

4. The process of claim 1 wherein the solid mixture of oxygen-containing benzenes and toluenes also contains cobalt and manganese salts of organic acids, organic bromides and inorganic bromides.

5. The process of claim 4 wherein the bed of particulated solid is a bed of silica sand and nitrogen is the gas flowing therethrough to stimulate said movement of particles.

6. The process of claim 4 wherein the bed of particulated solid is a bed of silica sand, a mixture of nitrogen and air comprises the gas flowing through the bed to stimulate said movement of particles.

7. The process of claim 5 or 6 wherein the gaseous product of pyrolysis is cooled to a temperature below the boiling point temperature of benzene, the resulting condensate of aromatic compounds is collected.

8. The process of claim 5 or 6 wherein the gaseous product of pyrolysis is cooled to a temperature below the boiling point of benzene, the resulting condensate of aromatic compounds is collected and the remainder of the gaseous product is burned to provide heat for the pyrolysis.

9. The process of claim 4 wherein the bed of particulated solid is a bed of silica and air enriched with oxygen gas and water vapor flowing through the bed stimulate said movement of particles.

10. The process of claim 4 wherein the bed of particulated solid is a bed of silica sand and the movement of its particles is stimulated by oxygen gas and water vapor.

* * * * *

UNITED STATES PATENT OFFICE
CERTIFICATE OF CORRECTION

Patent No. 4,393,264　　　　　Dated July 12, 1983

Inventor(s) John K. Allen and Gerard C. Lammers

It is certified that error appears in the above-identified patent and that said Letters Patent are hereby corrected as shown below:

| Col. | Line | |
|---|---|---|
| 2 | 54 | "decaboxylated" should read --decarboxylated-- |
| 3 | 26 | "boar" should read --boat-- |
| 4 | 68 | --"-- should read --do-- |
| 5 | 25 | "-008$^{(1,2,)}$" should read "-008$^{(1,2)}$" |
| 7 | 17 | "enbullient" should read --ebullient-- |
| 10 | 64 | "and particles" should read --sand particles-- |
| 11 | 24 | "thaf" should read --that-- |
| 11 | 63 | "$C_6C_6$, wt. %" should read --$C_6H_6$, wt. %-- |

UNITED STATES PATENT OFFICE
CERTIFICATE OF CORRECTION

Patent No. 4,393,264  Dated July 12, 1983

Inventor(s) John K. Allen and Gerard C. Lammers

It is certified that error appears in the above-identified patent and that said Letters Patent are hereby corrected as shown below:

Col. Line 13  20  "Benzene 9.35 wt. %  Benzene 10.99 wt. %  Benzene 17.2 wt. %" should read
"Benzene 9.35 wt. %  Benzene 10.99 wt. %  Benzene 17.2 wt. %"

14  37  "stimulate" should read --to stimulate--

Signed and Sealed this

Thirteenth Day of November 1984

[SEAL]

Attest:

Attesting Officer

GERALD J. MOSSINGHOFF

Commissioner of Patents and Trademarks